United States Patent [19]

Palmer et al.

[11] Patent Number: 5,454,378
[45] Date of Patent: Oct. 3, 1995

[54] BIOPSY FORCEPS HAVING A DETACHABLE PROXIMAL HANDLE AND DISTAL JAWS

[75] Inventors: Matthew A. Palmer; John R. Whittier; Sergio Rodriguez, all of Miami; Charles R. Slater, Fort Lauderdale, all of Fla.

[73] Assignee: Symbiosis Corporation, Miami, Fla.

[21] Appl. No.: 42,606

[22] Filed: Apr. 2, 1993

Related U.S. Application Data

[63] Continuation-in-part of Ser. No. 16,596, Feb. 11, 1993, and a continuation-in-part of Ser. No. 16,595, Feb. 11, 1993, abandoned.

[51] Int. Cl.⁶ .................................................. A61B 10/00
[52] U.S. Cl. ............................................. 128/751; 606/205
[58] Field of Search ................................ 128/749, 751; 606/205–208, 170–171, 142, 190; 16/114 R, DIG. 12, DIG. 24, DIG. 41, DIG. 42; 7/167; 30/329; 403/DIG. 4

[56] References Cited

U.S. PATENT DOCUMENTS

| | | | |
|---|---|---|---|
| 1,827,188 | 8/1925 | Burgess | 403/DIG. 4 X |
| 1,954,048 | 4/1934 | Jeffrey et al. | 403/DIG. 4 X |
| 2,790,437 | 4/1957 | Moore | 128/2 |
| 4,043,323 | 8/1977 | Komiya | 128/4 |
| 4,763,668 | 8/1988 | Macek et al. | 128/751 |
| 4,896,678 | 1/1990 | Ogawa | 128/751 |
| 5,094,247 | 3/1992 | Hernandez et al. | 128/751 |
| 5,100,430 | 3/1992 | Avellanet et al. | 128/751 X |
| 5,152,779 | 10/1992 | Sanagi | 606/205 |
| 5,217,479 | 6/1993 | Shuler | 128/751 X |
| 5,282,800 | 2/1994 | Foshee et al. | 606/52 |
| 5,282,806 | 2/1994 | Haber et al. | 606/139 |
| 5,290,308 | 3/1994 | Knight et al. | 606/207 X |
| 5,314,424 | 5/1994 | Nicholas | 606/208 X |
| 5,320,627 | 6/1994 | Sorensen et al. | 128/751 X |

FOREIGN PATENT DOCUMENTS

| | | | |
|---|---|---|---|
| 66465 | 12/1982 | European Pat. Off. | A61B 10/00 |

*Primary Examiner*—Lee S. Cohen
*Assistant Examiner*—Samuel Gilbert
*Attorney, Agent, or Firm*—David P. Gordon

[57] ABSTRACT

An endoscopic biopsy forceps has a detachable proximal handle portion and a distal portion which includes a pair of jaws mounted at the distal end of a flexible conduit. At least one pull wire extends through the conduit and is coupled to the jaws so that movement of the pull wire(s) through the conduit causes the jaws to open and close. The proximal end of the pull wire(s) is provided with a mating tip and the proximal end of the conduit is provided with a mating sleeve. The handle portion includes a shaft and a spool. The conduit is detachably attached to the shaft, while the pull wire(s) is detachably attached to the spool. Attachment is effected by spring biased coupling devices which engage the mating tip of the pull wire(s) and the mating sleeve of the conduit.

48 Claims, 10 Drawing Sheets

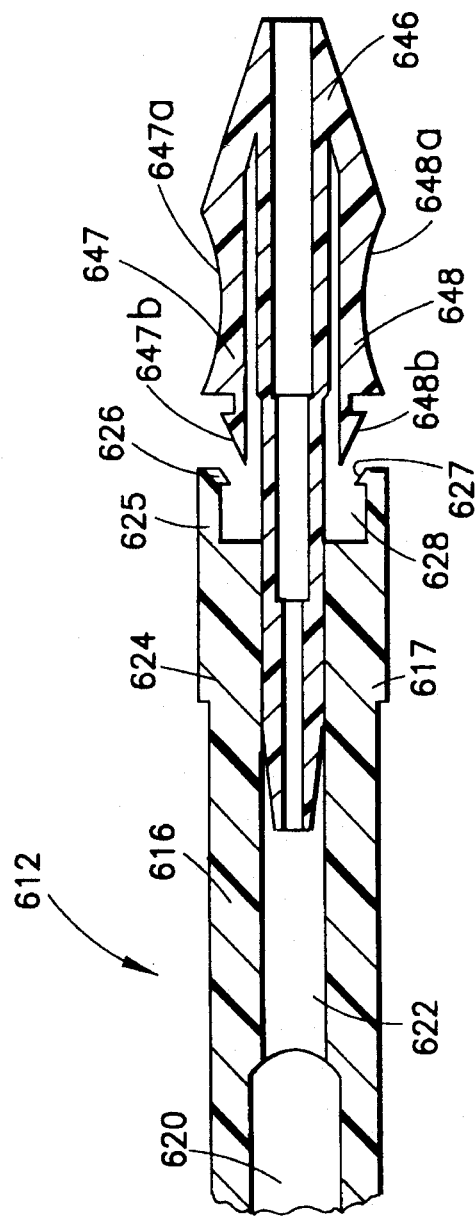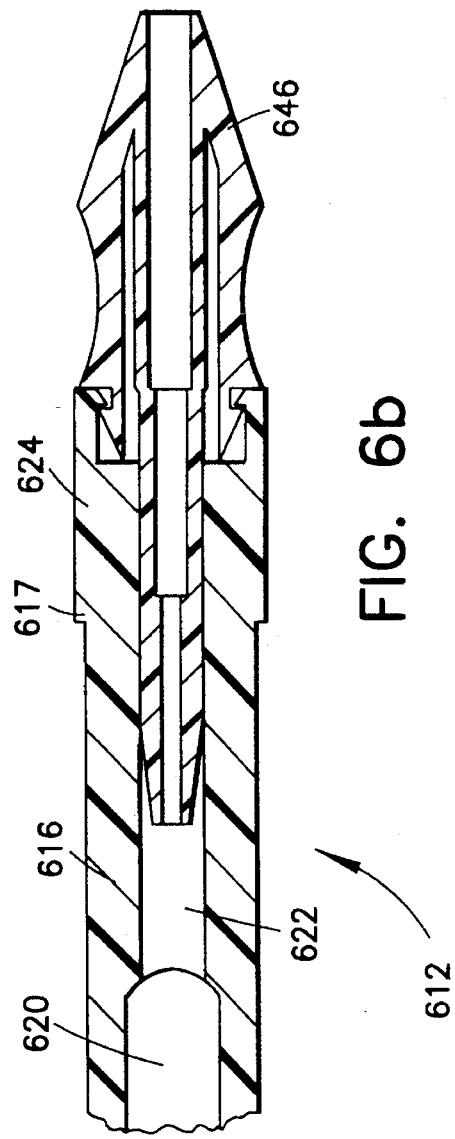

BIOPSY FORCEPS HAVING A DETACHABLE PROXIMAL HANDLE AND DISTAL JAWS

This application is a continuation-in-part of patent application Ser. No. 08/016,596 (Endoscopic Instruments Having Detachable Proximal Handle and Distal Portions) and Ser. No. 08/016,595, abandoned (Endoscopic Biopsy Forceps Devices with Selective Bipolar Cautery) both filed Feb. 11, 1993, and both of which are hereby incorporated by reference in their entireties herein.

BACKGROUND OF THE INVENTION

1. Field of the Invention

This invention relates to endoscopic surgical instruments. More particularly, the present invention relates to a surgical endoscopic biopsy forceps device having detachable proximal handle and distal portions.

2. State of the Art

Endoscopic surgery is widely practiced throughout the world today and its acceptance is growing rapidly. In general, endoscopic surgery involves the use of a camera or magnifying lens inserted through a tube, while a cutter, dissector, or other surgical instrument is inserted through another tube for purposes of manipulating and/or cutting an internal organ or tissue under view of the surgeon. In endoscopic biopsy procedures, typically, the camera is located in one lumen of a flexible endoscope while the biopsy cutter is placed through another lumen thereof.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. (As used herein, "proximal" means closest to the surgeon and farthest from the surgical site, while "distal" means farthest from the surgeon and closest to the surgical site.) The end effectors take many forms such as grippers, cutters, forceps, dissectors and the like.

Initially, endoscopic surgical instruments were very expensive, partly because they must be very small but still durable and reliable and the materials and manufacturing methods necessary to provide these features are expensive. Recently, however, a number of "disposable" endoscopic instruments have been introduced and their use is now widely accepted. One of the advantages of disposable endoscopic instruments over reusable instruments is that because they are used only a single time, there are no sterilization problems, (i.e., no risk of cross-contamination between patients) and no concerns about the dulling or nicking of blades or wearing of parts. However, in order to justify disposing of instruments after a single use, the instruments have to be much less expensive than the reusable tools. In order to manufacture the instruments less expensively, the disposable instruments therefore use less expensive materials. As a result, the disposable instruments potentially are less durable than the reusable instruments. It is recognized, however, that the less durable components of the disposable instruments are most often parts of the distal end effectors and that the proximal handle portion of a disposable instrument is substantially as durable as the proximal handle portion of a reusable instrument. Moreover, the distal end effectors are not so fragile that they can only withstand a single use. Despite manufacturer's recommendations to the contrary, some surgeons will sterilize disposable instruments and reuse them a few times in order to reduce "per procedure costs". Ultimately, however, it is the distal portion of the instrument which wears or breaks and mandates disposal of the entire disposable instrument.

Among the disposable endoscopic instruments in use today are a number of different types of biopsy forceps devices. These devices most often include very sharp opposing jaws for grasping and tearing tissue for biopsy. The jaws are mated with one another about a clevis pin which is mounted in a clevis. The clevis extends into a housing which is crimped to the distal end of a relatively long flexible coil. The proximal end of the coil is coupled to a handle having means for articulating the jaws. The handle generally includes a central slotted shaft about which a spool is disposed. A pull wire from the jaws extends through the coil and is attached to the spool while the coil is attached to the central shaft of the handle. Movement of the spool relative to the central shaft moves the pull wire relative to the coil and thus articulates the jaws at the distal end of the coil. In use, the jaws and coil are inserted through a flexible endoscope which is already in place in the patient's body. The surgeon guides the coil and jaws to the biopsy site while a nurse holds the handle. When the surgeon has located the jaws at the appropriate place, the nurse is instructed to operate the handle to articulate the jaws and grasp a biopsy sample. At the conclusion of the biopsy procedure, the entire forceps apparatus is either disposed of or sterilized for re-use.

The known endoscopic biopsy forceps devices of the art have the drawback that the jaws wear out long before the useful life of the handle has expired. Thus, the entire instrument must be discarded when it is only a small portion of the instrument which is inoperative.

Co-assigned parent application Ser. No. 08/016,596 discloses endoscopic instruments having detachable proximal handle and distal portions. These instruments have a distal assembly insertable and removable from a proximal handle assembly in one step actions. The distal assembly includes a tube, end effectors coupled to the tube, and a push rod coupled to the end effectors and slidable through the tube. The proximal handle assembly includes a tube sleeve for receiving the tube, manually operable actuating means, and a latch for coupling the push rod to the actuating means. The tube sleeve is provided with a ball or blade lock for holding the tube securely in place and the tube is provided with a circumferential groove for engaging the ball or blade lock. The latch is spring loaded, hinged, and has an inclined surface for quick coupling with the push rod and an unlatching surface which when biased by an unlatching member uncouples the push rod. The push rod is provided with a mating tip which engages the latch so that the manually operable actuating means causes reciprocal movement of the push rod within the tube to operate the end effectors. Coupling and uncoupling the proximal and distal assemblies is quick, one step, and substantially automatic.

A biopsy forceps device with detachable proximal handle and distal portions is also known and described in U.S. Pat. No. 4,763,668 to Macek et al. It is a disadvantage of the Macek et al. detachable biopsy forceps device that attachment and detachment of the proximal and distal portions requires the screwing in and out of screws and the rotation of a sleeve which makes the attachment and detachment procedures cumbersome. Indeed, no endoscopic instrument devices presently are known (except for that disclosed in the parent application hereto), which have a substantially one step coupling and decoupling mechanism.

SUMMARY OF THE INVENTION

It is therefore an object of the invention to provide a endoscopic biopsy forceps device where the proximal handle and the distal jaws are easily separable from each other so that the jaws may be discarded without disposing the handle.

It is also an object of the invention to provide an endoscopic biopsy forceps device where the proximal handle and the distal jaws are easily attachable to each other so that the handle may be re-used with a new set of jaws.

It is another object of the invention to provide an endoscopic biopsy forceps device where the proximal handle and the distal jaws of the device attach in substantially one step without the need for cumbersome manipulation of the device.

In accord with these objects which will be discussed in detail below, the biopsy forceps of the present invention includes a handle assembly and a coil and jaws assembly. The coil and jaws assembly has a distal pair of jaws mounted on a clevis and coupled to pull wires which run through the coil to its proximal end. The proximal end of the coil and jaws assembly is provided with coupling devices for removably coupling the coil and pull wires to the handle assembly. The handle assembly correspondingly includes coupling devices for removably coupling the handle to the coil and to the pull wires.

According to a preferred embodiment of the invention, the proximal end of the coil is provided with a mating sleeve having a circumferential groove, and the proximal ends of the pull wires are provided with a mating tip assembly. The handle assembly includes a central slotted shaft carrying a spool having a cross block which passes through the central slot of the shaft. The distal end of the shaft is provided with a spring biased latch for engaging the circumferential groove of the mating sleeve of the coil. The cross block of the spool is provided with a pair of spring biased sliders for engaging the mating tip assembly of the pull wires.

The mating sleeve has a tapered proximal end so that when it is inserted into the distal end of the handle shaft, the biased latch is moved open until the sleeve is inserted to the point where the circumferential groove is engaged by the latch. The cross block is provided with an internally tapered guide or funnel and the mating tip assembly of the pull wires is tapered to be received and guided by the guide. The sliders have angled faces (catches) for receiving the mating tip and locking around it. The coil and pull wires are thus coupled to the handle in a single motion by inserting the proximal end of the coil and pull wires into the distal end of the handle shaft. The mating sleeve and mating tip assembly automatically engage the latch and the sliders respectively and "snap" into place.

During disengagement, the latch is operated by a push button at the distal end of the handle shaft. By pushing the push button, the latch releases the coil and the circumferential groove of the mating sleeve can be slid out of engagement with the latch by pulling the coil. Pulling the coil from the handle also pulls the pull wires which are coupled to the cross block containing the sliders, which in turn results in a pulling of the cross block of the spool. As the cross block moves proximally along the slotted shaft, a collar or other mechanism is engaged by a mechanism attached to the proximal end of the slotted shaft or a protrusion located on the proximal end of the slotted shaft. The collar in turn engages angled extensions of the sliders, and forces the sliders apart, thereby releasing the mating tip assembly of the pull wires, and thus the handle from the distal assembly.

Additional objects and advantages of the invention will become apparent to those skilled in the art upon reference to the detailed description taken in conjunction with the provided figures.

BRIEF DESCRIPTION OF THE DRAWINGS

FIGS. 6a and 6b are cross sectional views of a coil sleeve and the distal end of a handle shaft in mating and non-mating positions in accord with yet another embodiment of the invention.

DETAILED DESCRIPTION OF THE PREFERRED EMBODIMENTS

Figure 1:
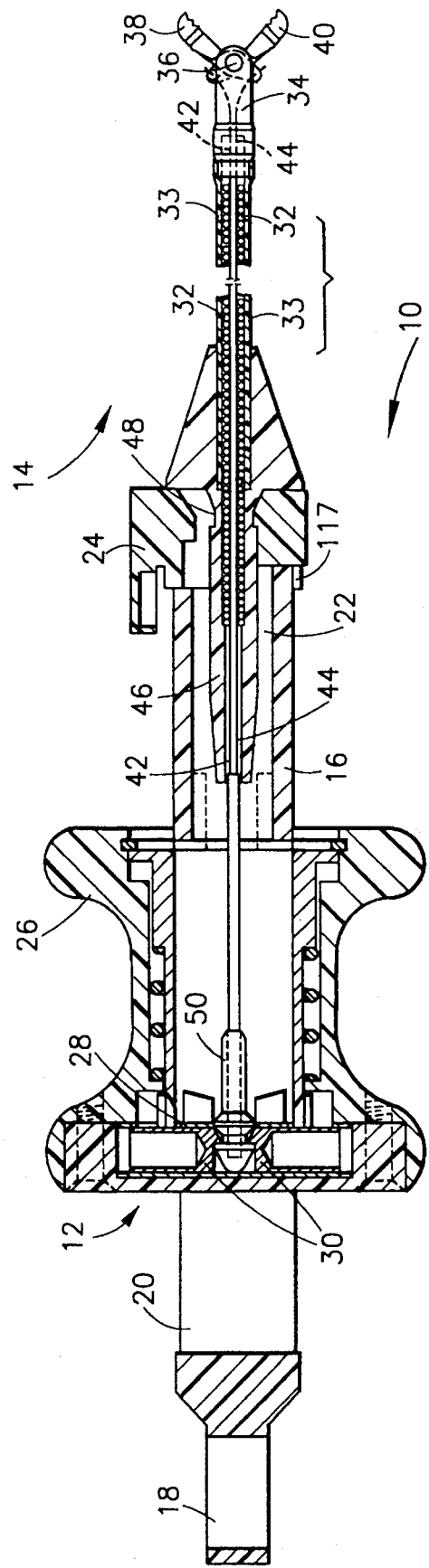
FIG. 1 is a cross sectional view of a first embodiment of the biopsy forceps according to the invention, with the distal end shown as a transparent side elevational view.
Figure 1A:
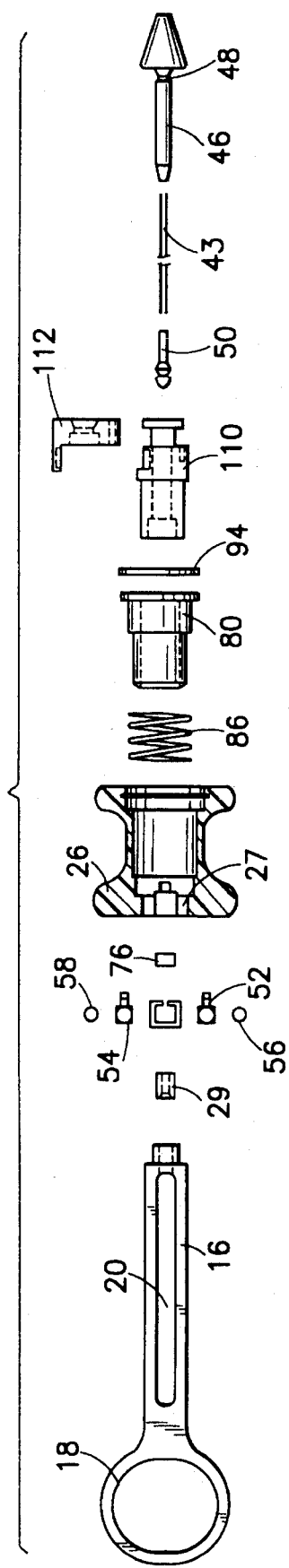
FIGS. 1a and 1b are exploded top and side views of the handle portion and the distal end portion coupling means of FIG. 1, with the coil coupling means rotated ninety degrees relative to FIG. 1.
Figure 1B:
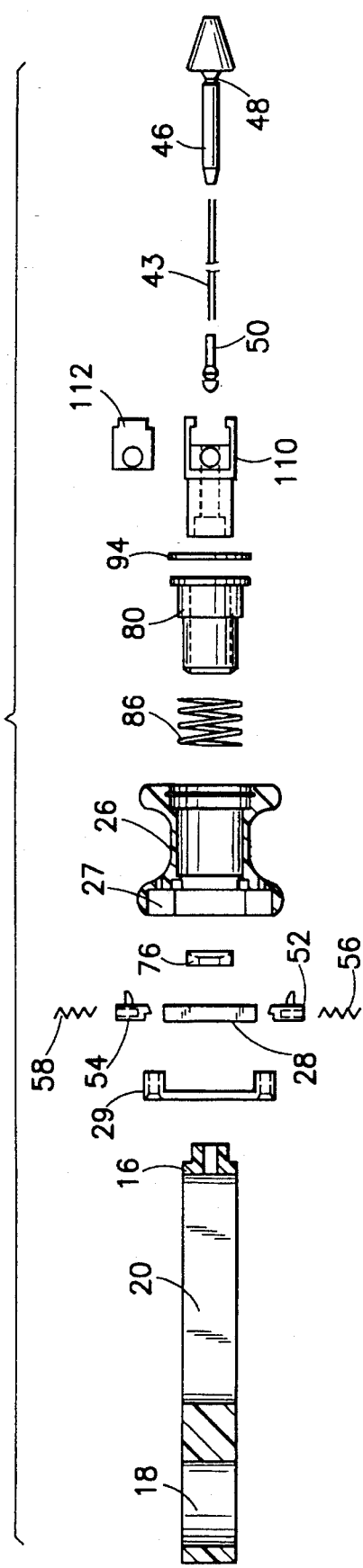

Referring now to FIGS. 1 and 1a, the endoscopic biopsy forceps 10 of the invention generally includes a proximal handle portion 12 and a detachable distal portion 14. The handle portion 12 generally includes a slotted shaft 16 having a proximal thumb ring 18, a central slot 20, a through bore 22, and distal coil coupling means 24 (shown schematically in FIG. 1). A displaceable spool 26 is disposed about the shaft 16. The spool is provided with a cross block 28 which passes through the central slot 20. Cross block 28 is provided with pull wire coupling means 30 (shown schematically in FIG. 1).

The distal portion 14 of the endoscopic biopsy forceps device includes a coil 32 which is typically several feet in length and is typically covered at least in part by a strain relief tube 33. The distal end of the coil is preferably provided with a clevis 34 having a clevis pin 36 carrying a pair of opposed jaws 38, 40 which are mounted for rotation about the clevis pin 36. In the preferred embodiment, two pull wires 42, 44 are attached to the jaws and extend through the coil. The proximal end of the coil is provided with a mating sleeve 46 having a circumferential groove 48. Pull wires 42, 44 extend through the the mating sleeve and terminate with a mating tip assembly 50.

As shown in FIG. 1, the handle portion 12 and the distal portion 14 of the biopsy forceps device are coupled by the coil coupling means 24 engaging the circumferential groove 48 of the mating sleeve 46 of the coil 32 and by the pull wire coupling means 30 engaging the mating tip assembly 50 of the pull wires. In the assembled condition shown in FIG. 1, movement of the spool 26 relative to the shaft 16 moves the pull wires 42, 44 through the coil 32 to open or close the jaws 38, 40 at the distal end of coil 32. As will be appreciated by those skilled in the art, the forceps are most commonly operated by inserting one's thumb through the thumb ring 18 and moving the spool with one's index and middle fingers in a manner similar to the operation of a hypodermic syringe.

Figure 2:
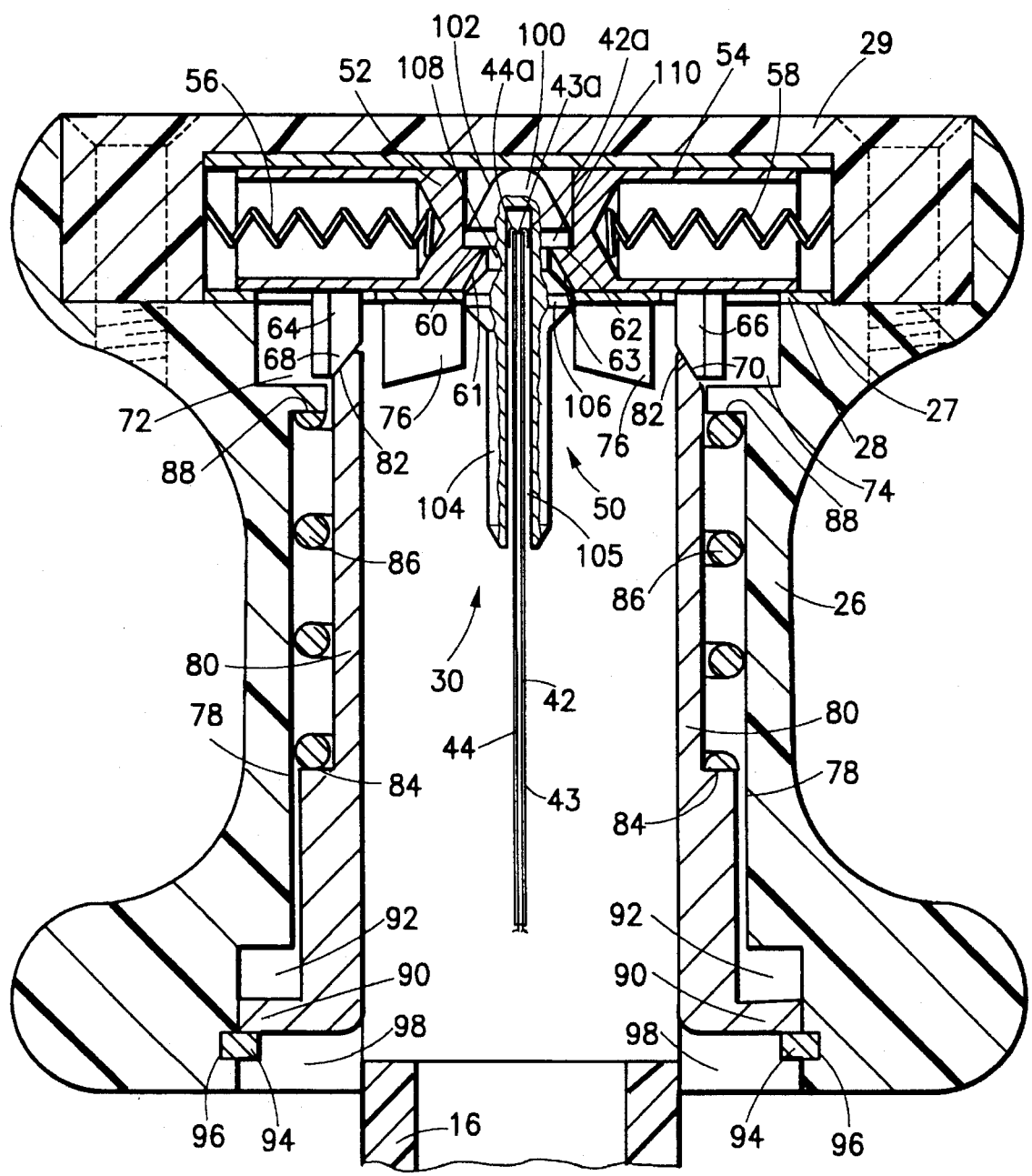
FIG. 2 is a cross sectional view of a first embodiment of pull wire coupling device with pull wire mating tip assembly coupled thereto.

Turning now to FIG. 2, the pull wire coupling means 30 and mating tip assembly 50 are shown in greater detail. As seen in FIG. 2, the spool 26 is provided with an upper recess 27 which receives the cross block 28. The cross block is held in place by a top cover 29 which is retained in the spool with screws (not shown). The cross block 28 is provided with a pair of opposed sliders 52, 54 biased inwardly by springs 56, 58. It will be appreciated that only one slider is necessary, although two are preferred. The operative end of each slider is provided with a shoulder catch 60, 62 with an angled entry 61, 63 and the bottom of each slider is provided with a downward extending tang 64, 66 having an angled end 68, 70. Recesses 72, 74 in the spool 26 are provided for permitting outward movement of the slider tangs as described below, and may be provided as individual recesses or as a single annular recess in the spool. A central guide (funnel) 76 extends proximally from the cross block 28, and may be manufactured integrally therewith if desired. The guide guides the mating tip 50 during entry and exit from the cross block as will be described in detail below.

Figure 2A:
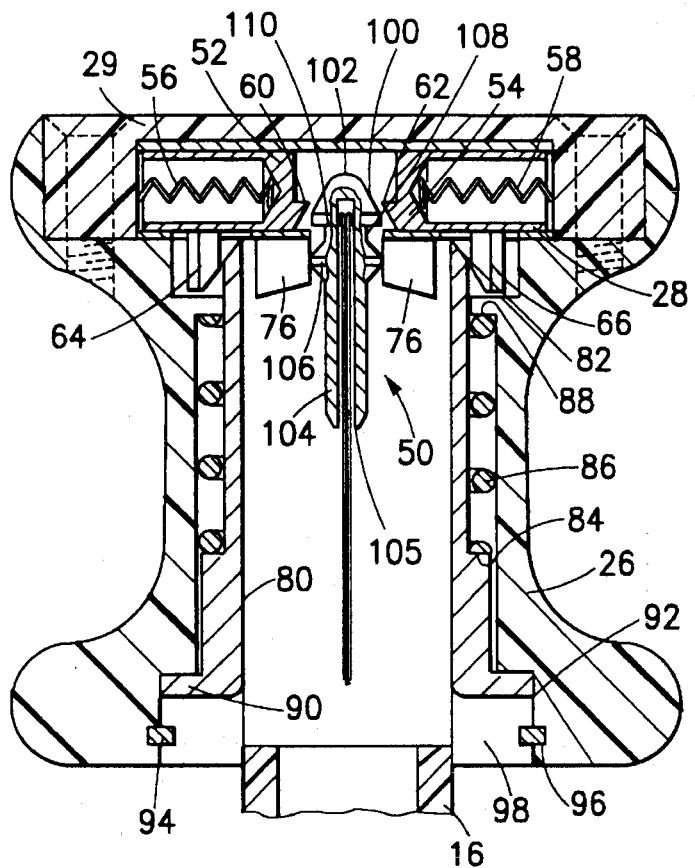
FIG. 2a is a view similar to FIG. 2 showing the mating tip uncoupled from the coupling device.

In the embodiment of FIGS. 2 and 2a, the spool 26 is provided with a central bore 78 which houses a spring biased collar 80. Collar 80 has an inclined annular proximal edge 82, a middle shoulder 84, and a distal flange 90. A collar spring 86 surrounds the collar 80 and rests at one end against the middle shoulder 84. The other end of the spring 86 rests against an upper shoulder 88 in the central bore 78 of the spool 26. Spring 86 thereby biases the collar 80 away from the angled ends 68, 70 of the slider tangs 64, 66. The distal flange 90 of the collar 80 is received in a wider recess 92 in the central bore 78 of the spool 26. The biased collar 80 is held within the spool 26 by a snap ring 94 which is received in a groove 96 in the spool 26. The snap ring 94 engages the flange 90 of the collar 80 while leaving an annular space or opening 98 between the outer diameter of the handle shaft 16 and the inner diameter of the snap ring 94. It is through the opening 98 that a protrusion on the handle can be extended, as described below, in order to engage the collar 80 so as to overcome the bias of the spring 86.

As seen in FIGS. 2 and 2a, the mating tip assembly 50 comprises a conical head 100 with a spherical apex 102, a base shaft 104 with a central bore 105, and a ring 106. The ring 106 together with the base 110 of the conical head 100 define a groove 108. The pull wires 42, 44 covered with the anti-kinking tube 43 are inserted into the central bore 105 of the base shaft 104 of the mating tip 50. According to a preferred embodiment of the invention, the proximal ends 42a, 44a of pull wires 42, 44 are bent over the proximal end 43a of the anti-kinking tube 43 prior to insertion into the central bore 105, and the shaft may be crimped to prevent the pull wires from escaping.

It will be appreciated that during assembly, the coupling of the mating tip 50 with the sliders 52, 54 is easily accomplished by pushing the conical head 100 of the tip assembly 50 against the angled entries 61, 63 of the shoulder catches 60, 62 of the sliders 52, 54, guided by guide funnel 76. This action causes the sliders to slide outward against springs 56, 58 and allow the head 100 of the mating tip 50 to pass into the cross block 28 whereupon, the shoulder catches 60, 62 of the sliders 52, 54 are biased inward into the space 108 between the head 100 and the ring 106. When assembled, and during use, and as seen in FIG. 2, the shoulder catches 60, 62 of the sliders 52, 54 engage the space 108 along the base shaft 104 between the base 110 of the head 100 and the ring 106. After use, when it is desired to uncouple the handle portion of the biopsy forceps device from the distal portion, uncoupling of the mating tip from the sliders is accomplished by moving the collar 80 against spring 86 until the upper edge 82 of collar 80 engages the angled ends 68, 70 of slider tangs 64, 66. The engagement of the collar edge 82 with the ends 68, 70 of the tangs forces the sliders to move outward against their respective springs, thereby removing the shoulder catches from beneath the head 100 of the mating tip assembly 50. This allows the mating tip to be removed from the cross block as shown in FIG. 2a. Actuation of the sliding collar is described in detail below.

Figure 2B:
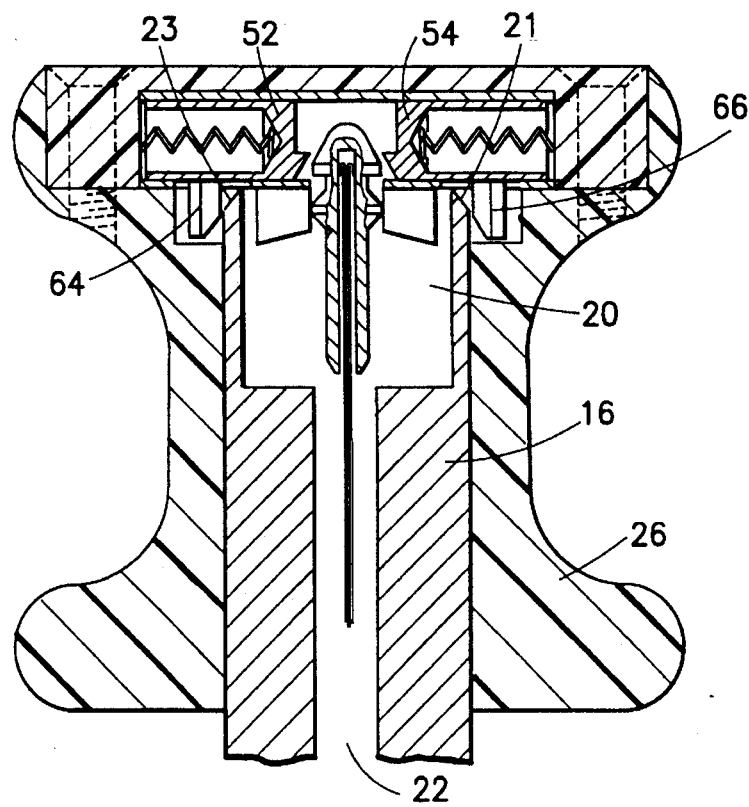
FIG. 2b is a view similar to FIG. 2 of a second embodiment of pull wire uncoupling device.

FIG. 2b shows a different embodiment of the uncoupling mechanism in which the sliding collar is replaced by an angled edges 21,23 or protrusions of the shaft 16 at the distal end of the slot 20. As the spool is moved toward the distal end of the handle, the angled edges of the shaft engages the tangs 64, 66 of the sliders 52, 54 in a manner similar to the engagement by the collar 80 in FIGS. 2 and 2a. It will be appreciated that the spool is prevented from moving to the distal end of the slot so long as the mating sleeve of the coil is coupled to the handle (FIG. 1). That is, there is always a minimum length of pull 16 wire extending from the end of the coil (when the jaws are opened) and this length is sufficient to prevent the movement of the spool to the distal point where the tangs of the sliders will be engaged by the edges of the shaft as shown in FIG. 2b. Only upon releasing the mating sleeve of the coil will the spool be free to move to the distal point where release of the pull wires will be effected.

Figure 2C:
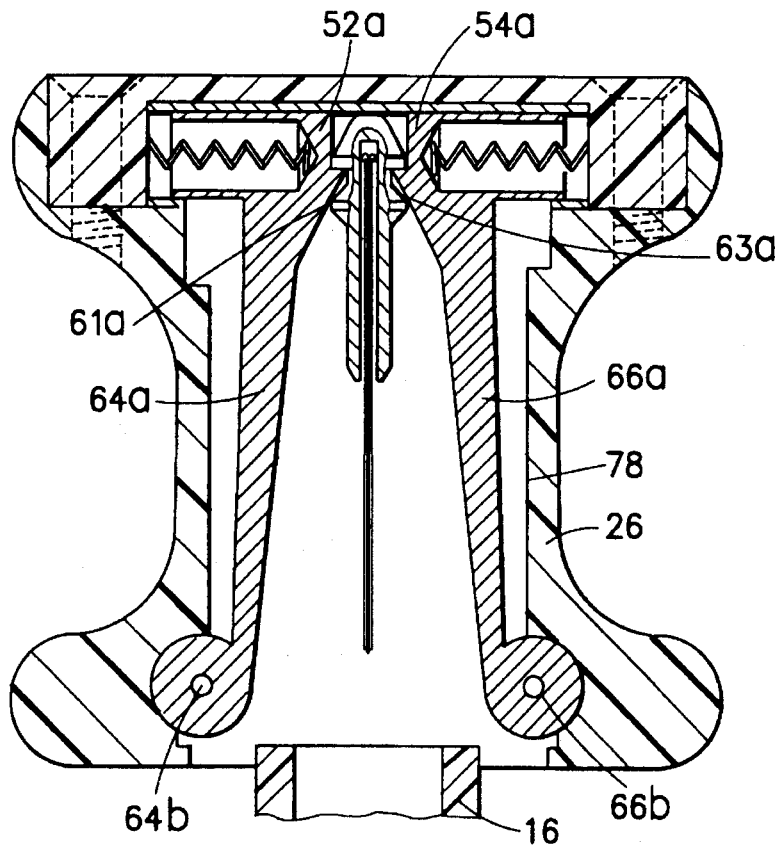
FIG. 2c is a view similar to FIG. 2 of another embodiment of pull wire coupling and uncoupling device.

FIG. 2c shows another embodiment of the pull wire coupling device where the tangs 64a, 66a of the "sliders" 52a, 54a extend as arms to lower pivot points 64b, 66b in the spool. This embodiment has the advantage that tolerance need not be so strict, as instead of the disengaging mechanism being dependent on sliders which slide in a housing, the pivot arrangement allows for substantially axial movement of the sliders without requiring a close fitting housing. In addition, without the closely fitting slider housing, the mechanism is not as easily clogged. Release of the pivot sliders in this embodiment may be by a collar or by the mechanism described with reference to FIG. 2b.

Figure 2F:
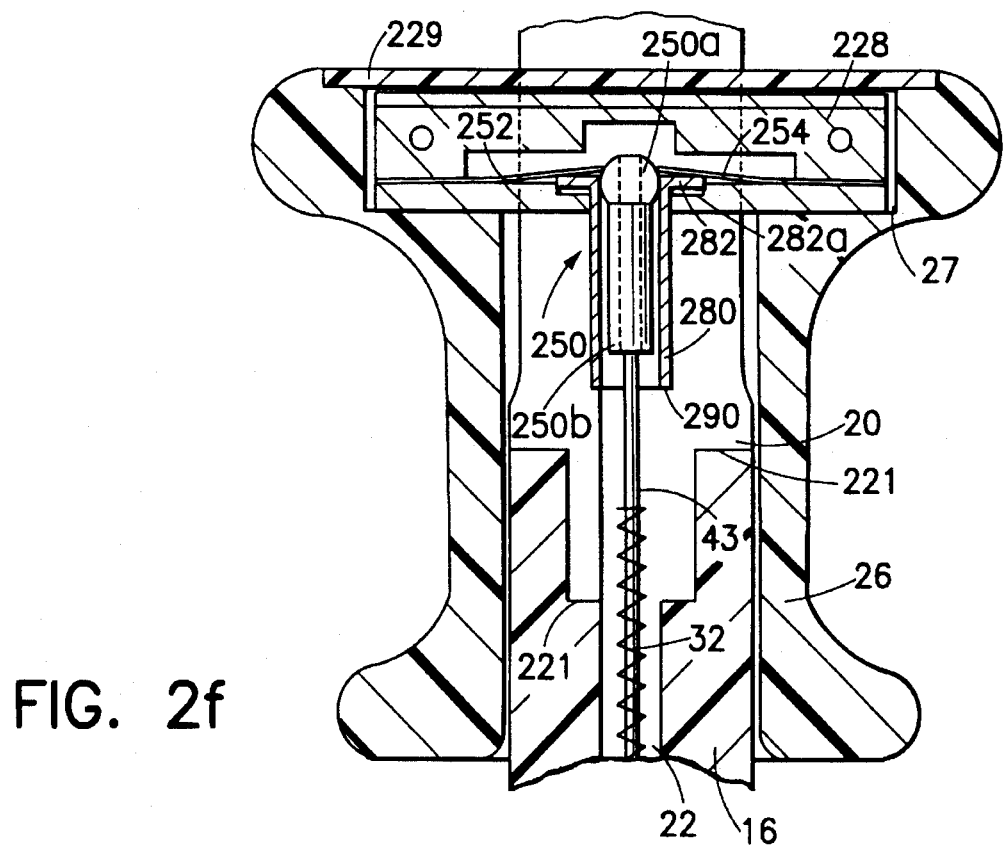
FIG. 2f is a cross sectional view of another embodiment of the pull wire coupling/uncoupling device.
Figure 2D:
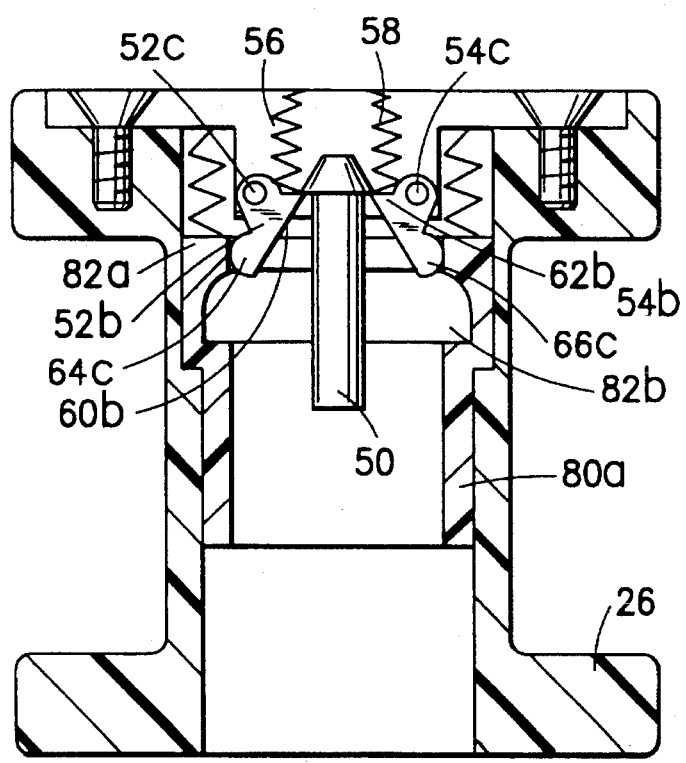
FIG. 2d is a simplified cross sectional view of another embodiment of pull wire coupling/uncoupling device with pull wire mating tip coupled thereto.
Figure 2E:
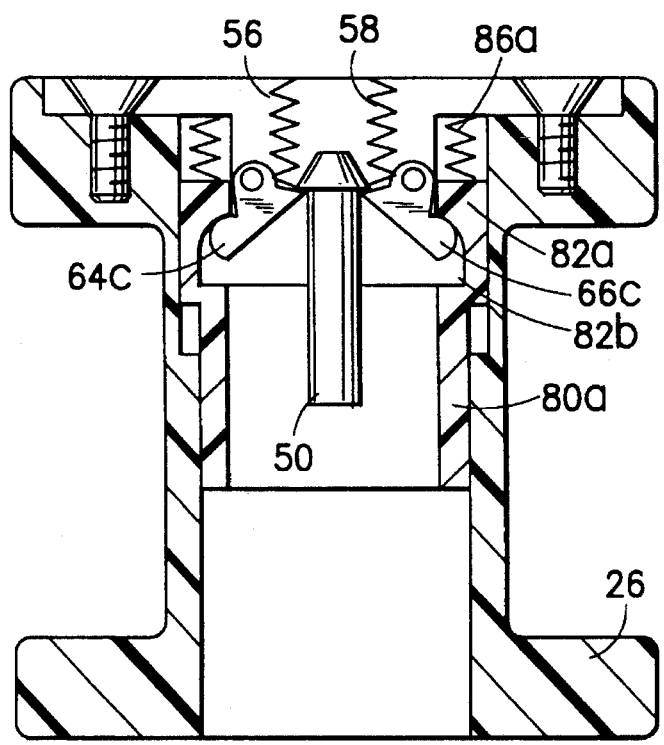
FIG. 2e is a view similar to FIG. 2d showing the mating tip uncoupled from the coupling device.
Figure 3:
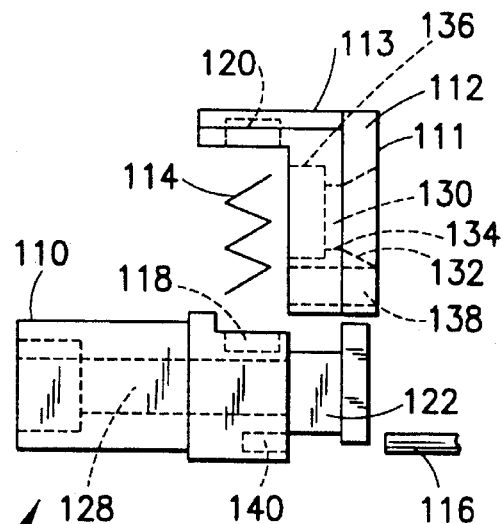
FIG. 3 is a side elevation exploded view of a first embodiment of coil coupling device.
Figure 3A:
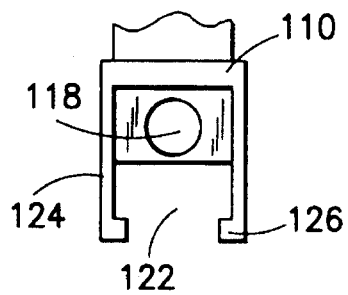
FIG. 3a is a top view of the stationary portion of the coupling device of FIG. 3.
Figure 3B:
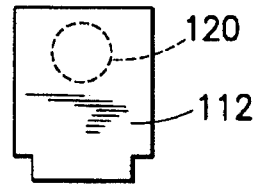
FIG. 3b is a top view of the sliding portion of the coupling device of FIG. 3.
Figure 3C:
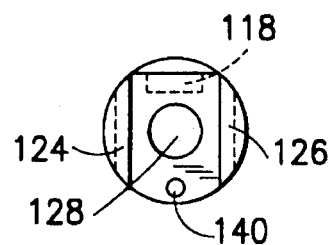
FIG. 3c is a distal end view of the stationary portion of the coupling device of FIG. 3.
Figure 3D:
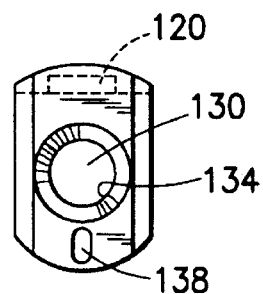
FIG. 3d is a distal end view of the sliding portion of the coupling device of FIG. 3.

FIGS. 2d and 2e show yet another embodiment of pull wire coupling means where the sliders are replaced by pivoting catches 52b, 54b which pivot on axes 52c, 54c. Catches 52b, 54b are biased by springs 56, 58 to an open position shown in FIG. 2e. Pivoting of the catches is limited by a sliding collar 80a which engages lower ends (lobes) 64c, 66c of the catches. Collar 80a has an upper engaging edge 82a and an adjacent receiving space 82b. Spring 86a biases the collar 80a in a distal direction so that its upper engaging edge 82a engages the lower ends 64c, 66c of the catches 52b, 54b as shown in FIG. 2d. In this position, the mating tip 50 may be inserted between the catches where the conical portion of the mating tip moves the catches against springs 56, 58 until the tip 50 snaps into place behind the catches as shown in FIG. 2d. The mating tip 50 is released by moving the collar 80a in the proximal direction as shown in FIG. 2e so that the lobes 64c, 66c of the catches 52b, 54b are no longer engaged by the upper edge 82a and are free to move under the bias of springs 56, 58 into the receiving space 82b.

FIG. 2f shows yet another embodiment of pull wire coupling/uncoupling means. In this embodiment, cross block 228 residing in upper (proximal) recess 27 of spool 26 contains a pair of leaf springs 252, 254 which engage mating tip 250 in a manner similar to the embodiment shown in FIG. 2. In particular, when mating tip 250 having a head 250a and a shaft 250b enters the cross block 228, the leaf springs 252, 254 are pushed apart by the head 250a of the mating tip. After the mating tip head 250a has entered a sufficient distance into the cross block 228, the leaf springs spring back to engage the shaft 250b of the mating tip 250 just below the head 250a. Uncoupling of the mating is accomplished by a sliding collar 280 having a proximal flange 282 and a distal end 290. The flange 282 of collar 280 is held in a recess 282a of the cross block. It will be appreciated that, upon mating, the collar 280 is substantially coaxial with the mating tip 250. Movement of the collar 280 in a proximal direction relative to the cross block causes the flange of the collar to push against the leaf springs and spread them apart from the mating tip as seen in FIG. 2f. Movement of the collar to uncouple the mating tip is effected in a manner similar to that described above. Here, however, when the spool is moved towards the distal end of the handle, the distal end 290 of the collar is engaged by a shoulder 221 formed by a step in the throughbore 22.

Figure 4A:
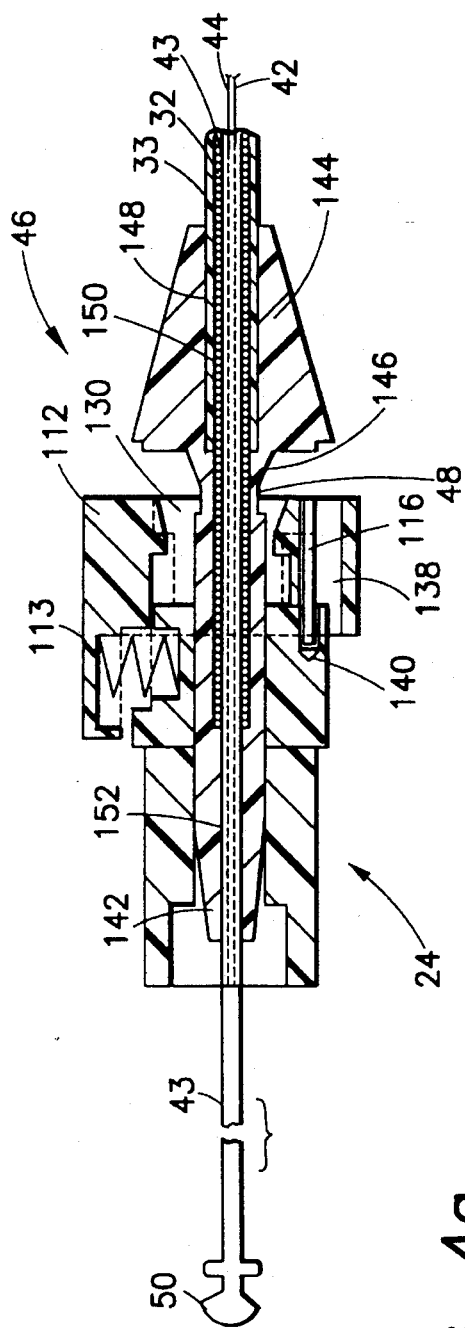
FIG. 4a is a cross sectional view of the assembled coupling device of FIG. 3 with a coil mating sleeve partially inserted.
Figure 4B:
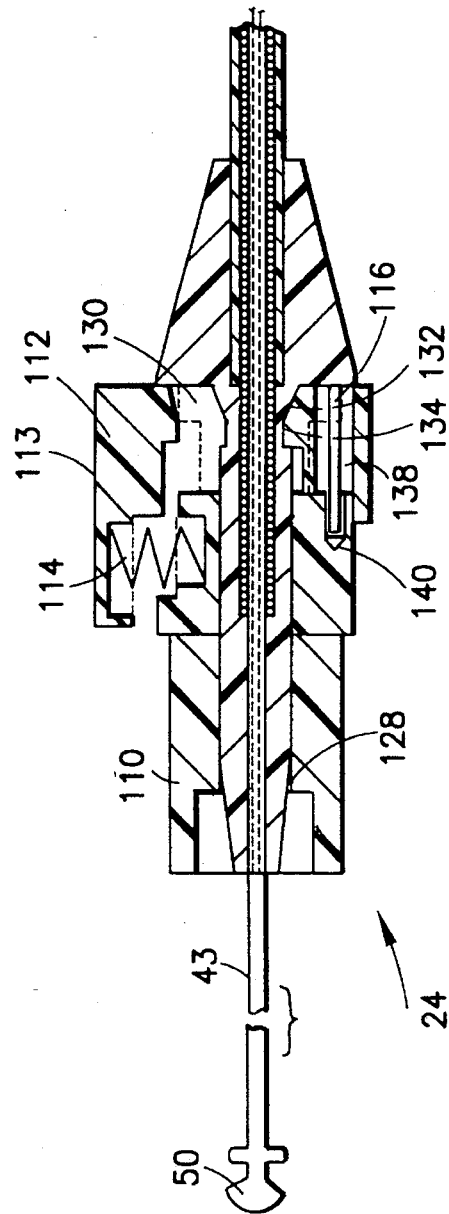
FIG. 4b is a view similar to FIG. 4a but with the coil mating sleeve fully inserted and coupled thereto.

Turning now to FIGS. 3, and 3a-3d the coil coupling device 24 which is preferably integral with the shaft 16 of the handle 12 is shown in greater detail. The coil coupling device 24 detachably attaches the mating sleeve 46 (FIGS. 1, 4a and 4b) of the coil 32 with the distal end of the handle 12 as shown and described in detail below with reference to FIGS. 4a and 4b. The coil coupling device 24 includes a body 110, a latch 112, a spring 114, and a latch limit pin 116. The body 110 has a stepped shoulder 117, and an upper spring retaining bore 118, while the latch 112 has a lower spring retaining bore 120. Latch 112 has an upper horizontal portion 113 and a lower vertical portion 111 which is slidable through a "T" channel 122 defined by arms 124, 126 at the distal end of the body 110. The body 110 has a central throughbore 128 for receiving the mating sleeve 46 (FIGS. 1, 4a, and 4b). Vertical portion 111 of latch 112 has a central throughbore 130 with a ramped inlet 132, an inside rim 134, and a wide receiving space 136. An oblong pin receiving slot 138 is located beneath the throughbore 130 in the latch 112 and a pin mounting bore 140 is located below the throughbore 128 in the body 110. It will be appreciated from the foregoing description in conjunction with FIGS. 4a and 4b and the following description, that the coil coupling device 24 is assembled by placing the spring 114 into the retaining bore 118, sliding the latch 112 into the channel 122 of the body 110 so that the upper end of the spring 114 enters the retaining bore 120 of the latch 112, sliding the latch against the bias of the spring until the oblong pin receiving slot 138 aligns with the pin mounting bore 140, and inserting the pin 116 through the oblong slot 138 into the mounting bore 140. The size of the oblong slot 138 is dimensioned so that the latch 112 is slidable from a position where its bore 130 is substantially coaxial with the bore 128 in the body 110 to a biased off-center position where the inner rim 134 of the latch bore 130 obstructs the body bore 128. The resulting mechanism is similar to a blade lock such as described in parent application Ser. No. 08/016,596.

Turning now to FIGS. 4a and 4b, it will be seen that the mating sleeve 46 has a proximal tapered tip 142 and a distal collar 144. A circumferential groove 48 is arranged between the tip 142 and collar 144. It will be appreciated that the maximum outer diameter of the tip 142 is such that the mating sleeve fits comfortably within the bore 128 in the body 110 of the coil coupling device 24 as shown in FIGS. 4a and 4b. Between the groove 48 and the distal collar 144, the mating sleeve preferably has a flared wall 146. The profiles of the flared wall 146 and the groove 48 are dimensioned to mate with the ramped entrance 132 and the inside rim 134 of the latch 112. Mating sleeve 46 has a stepped central throughbore 148, 150, 152 of decreasing diameter from the distal to proximal ends of the mating sleeve. The largest diameter distal portion 148 receives the coil 32 covered with strain relief 33 and containing pull wires 42, 44 covered by anti-kinking tube 43. A smaller diameter middle portion of the bore 150 receives the coil 32 without the strain relief 33. The smallest diameter proximal portion 152 receives the pull wires covered by the anti-kinking tube 43. The anti-kinking tube 43 containing pull wires 42, 44 extends beyond the proximal end of the mating sleeve to the pull wire mating tip assembly 50 as described in detail above with reference to FIGS. 1 and 2.

Comparing FIGS. 4a and 4b and with reference to FIG. 1, it will be appreciated that a rapid substantially one step coupling of the handle 12 with the distal portion 14 is accomplished simply by inserting the proximal end of the distal portion into the distal end of the handle. The mating tip 50, anti-kinking tube 43, and tapered tip 142 of the mating sleeve 46 enter the bore 130 of the latch 112 which is biased to its off-center position by spring 114. Mating tip 50 is small enough to enter the bore 128 of the body 110 even when obstructed by the off-centered latch 112. The tapered tip 142 of the mating sleeve 46 engages the ramped entrance 132 of the latch 112 and moves the latch against the bias of spring 114 to a position where the latch bore 130 is substantially coaxial with the bore 128 of the body 110. As the mating sleeve 46 is pressed farther into the body 110, the mating tip 50 of the pull wires 43 engages the funnel described above with reference to FIG. 2. Depending on the position of the spool 26, the mating tip 50 may not be engaged by the sliders before the groove 48 in the mating sleeve 46 is engaged by the latch 112. If the mating sleeve 46 is coupled before the mating tip is coupled to the sliders, it is of no consequence since the mating tip will couple with the sliders as soon as the forceps are first used. In this regard, it should be recalled that movement of the pull wires in the distal direction opens the jaws and movement of the pull wires in the proximal direction closes the jaws. After the mating sleeve is coupled, movement of the spool in the distal direction to effect an opening of the jaws will couple the mating tip and the sliders, if such coupling has not yet been effected.

Referring now to FIGS. 1, 2, 4a and 4b, it will be appreciated how the distal portion 14 is rapidly uncoupled from the handle portion 12 in substantially a single motion. The horizontal portion 113 of latch 112 acts as a "release button" and is pressed in against the spring 114 moving the latch bore 130 into its substantially coaxial position with body bore 128 and thereby allowing the removal of mating sleeve 46. While the button is pressed in, the mating sleeve 46 is grasped by its distal collar 144 and pulled away from the handle 12. This action pulls the spool 26, which is still coupled to the mating tip 50 of the pull wires, towards the distal end of the handle. (In this regard, it is worth noting that the spool must not be grasped when uncoupling.) The stepped shoulder 117 of the body 110 of the coil coupling device 24 is then in a position to enter the annular space 98 at the base of spool 26 and engage the flange 90 of collar 80. As the spool is pulled farther against the latch, the collar 80 is moved against spring 86 until the upper edge 82 of collar 80 engages the tangs 66 of the sliders to move the sliders against their respective springs and release the mating tip 50. It will be appreciated that collar 80 could be engaged by any projection on the shaft 16 of the handle 12 and that a different configuration of the top horizontal portion 113 of the latch 112 could thus be used. Moreover, the collar, itself, need not be a spring biased part of the spool but could be provided as a stationary part of the handle shaft such that the tangs of the sliders are engaged when the spool is moved to a distal portion of the shaft as shown and described above with reference to FIGS. 2b and 2c.

Figure 5:
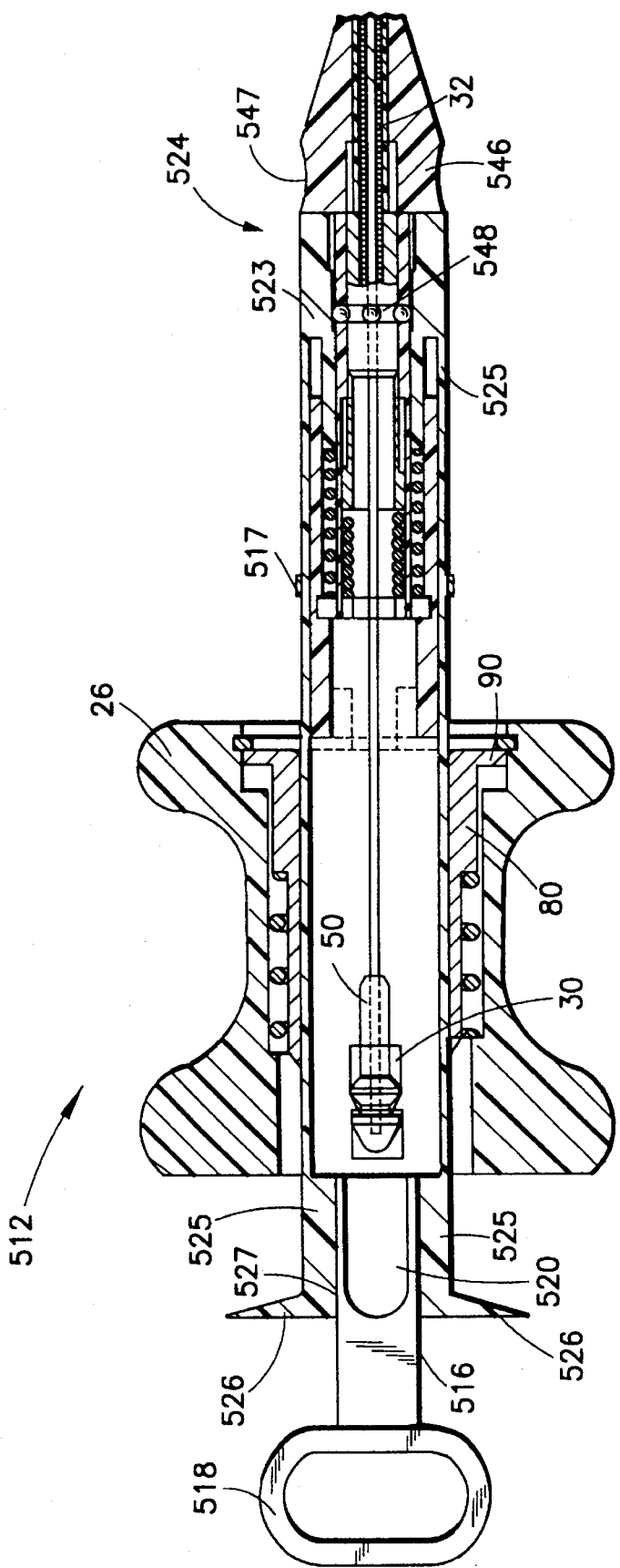
FIG. 5 is a cross sectional view similar to FIG. 1 showing an alternate embodiment of the coil coupling/uncoupling device.

Turning now to FIG. 5, an alternate embodiment of the coil coupling device 524 is shown on a slightly modified handle 512. Handle 512 includes a shaft 516 with a thumb ring 518 and a slot 520. The distal end of the shaft is provided with a coil coupling device 524 which is substantially the same as the ball bearing tube coupling device shown in parent application Ser. No. 08/016,596. The sliding collar 523 of the coil coupling device 524 is provided with an extension sleeve 525 which extends along the length of shaft 516 to a point between the spool 26 and the thumb ring 518 and terminates in a finger grip 526. It will be appreciated that the extension sleeve 525 is provided with a slot 527 which substantially coincides with slot 520 in the shaft 516. The spool 26 is fitted over the shaft 516 with the extension sleeve 525 interposed between the spool and the shaft. Operation of the pull wire coupling device 30 is substantially the same in this embodiment as in the embodiment of FIG. 1. However, the flange 90 of the collar 80 is engaged in this embodiment by step ring 527 on the extension sleeve 525. By reference to the cited parent application, those skilled in the art will appreciate that uncoupling of the coil coupling device 524 is effected by pulling the finger grip 526 towards the thumb ring 518 which slides the sliding collar 523 to release the ball bearings from groove 548 in the mating sleeve of the coil. The mating sleeve 546 is advantageously provided with a finger grip 546 so that after the coil coupling device is uncoupled, the coil and pull wires can be pulled from the handle.

Turning now to FIGS. 6a and 6b, an alternate embodiment of the coil coupling device 624 is shown on a slightly modified handle 612. Handle 612 includes a shaft 616 with a thumb ring (not shown), a throughbore 622, and a slot 620. The distal end of the shaft is provided with a coil coupling device 624 which includes an outer ring 625 having a lip 626 with an angled entry 627. Between the lip 626 and the throughbore 624 of the shaft is an annular space 628. The mating sleeve 646 of the coil (not shown) is provided with one or more resilient arms 647, 648. Each arm is advantageously provided with a finger grip 647a, 648a for squeezing the resilient arms. Moreover, each arm 647, 648 terminates with an angled barb 647b, 648b. Comparing FIGS. 6a and 6b, it will be appreciated that the mating sleeve is easily coupled to the coil coupling device in a simple one-step operation by inserting the sleeve into the coupling device. Upon insertion, the angled barbs engage the angled entry of the lip. The resiliency of the arms allows them to bend radially inward so that the barbs can cross the lip into the annular space. The same resiliency causes the barbs to spring radially outward into the annular space once they cross the lip. The barbs are thus secured within the annular space and the mating sleeve is effectively coupled to the coil coupling device. It will also be appreciate that by squeezing the finger grips 647a, 648a, the resilient arms are bent radially inward, and the barbs may be removed out from the annular space so that the sleeve can be removed from the coupling device by pulling. As with the embodiments described above, the shaft 616 is provided with a shoulder 617 for engaging the flange of the collar in the spool to uncouple the pull wires from the spool when the coil is removed from the coil coupling device.

There have been described and illustrated herein several embodiments of an endoscopic biopsy forceps having a detachable proximal handle and distal jaws. While particular embodiments of the invention have been described, it is not intended that the invention be limited thereto, as it is intended that the invention be as broad in scope as the art will allow and that the specification be read likewise. Thus, while particular pull wire and coil coupling means have been disclosed, it will be appreciated that other types of coupling means could be utilized provided that substantially single step coupling can be accomplished. Also, while particular mating sleeves and mating tips have been shown, it will be recognized that other types of mating means on the pull wires and coil could be used with similar results obtained. Moreover, while particular configurations have been disclosed in reference to the handle, it will be appreciated that other configurations could be used as well. Furthermore, while the handle has been disclosed as having a manually displaceable spool, it will be understood that different manual or automated means can achieve the same or similar function of moving the pullwire(s) through the coil to operate the distal jaws. The essence of the invention, therefore, is the provision of substantially one-step coupling of the coil and pull wire(s) to the handle by simple insertion and an easy uncoupling of the coil and pull wire(s) from the handle. It will therefore be appreciated by those skilled in the art that yet other modifications could be made to the provided invention without deviating from its spirit and scope as so claimed.

We claim:

1. An endoscopic biopsy forceps comprising:
   a) a flexible conduit having a proximal and a distal end, said proximal end of said conduit being provided with a first mating means for mating with a coupling means;
   b) a pair of jaws mounted at the distal end of said flexible conduit;
   c) at least one pull wire having a proximal and a distal end, the distal end of said pull wire being coupled to said pair of jaws, said pull wire extending through said conduit and said proximal end of said pull wire extending beyond said proximal end of said conduit, movement of said pull wire through said conduit effecting opening and closing of said jaws, said proximal end of said pull wire being provided with a second mating means for mating with a coupling means;

d) a handle having first coupling means for detachably attaching to said first mating means, and second coupling means for detachably attaching to said second mating means, handle including actuating means for moving said pull wire through said conduit, wherein, one of said first mating means and said first coupling means is spring biased, and one of said second mating means and said second coupling means is spring biased, such that insertion of said proximal end of said flexible conduit and said proximal end of said pull wire into said handle automatically couples said first mating means to said first coupling means and said second mating means is automatically coupled to said second coupling means upon one of said insertion and movement of said actuation means.

2. An endoscopic biopsy forceps according to claim 1, wherein:

said first coupling means is spring biased such that insertion of said first mating means into said first coupling means moves said first coupling means and couples said first mating means to said first coupling means.

3. An endoscopic biopsy forceps according to claim 2, wherein:

said handle includes a shaft and an annular movable member through which said shaft extends, said shaft having a transverse slot, said annular movable member having a transverse member extending through said slot such that said annular movable member is captured by said shaft, said transverse member includes said second coupling means, and said second coupling means comprises at least one leaf spring, and said second mating means includes a mating tip with a distal portion of smaller diameter than a proximal portion of said mating tip, wherein said leaf spring is bendable by said mating tip and engages said mating tip distal of said proximal portion of said mating tip.

4. An endoscopic biopsy forceps according to claim 2, wherein:

said first coupling means includes,
a first sliding member having a throughbore which receives said first mating means, said throughbore having an inner rim,
a body member having a central throughbore which receives said first mating means, and a channel which holds said first sliding member,
a spring which biases said first sliding member relative to said body member so that said inner rim partially obstructs said central throughbore of said body member, and wherein said first mating means comprises a sleeve having a circumferential groove which engages said inner rim.

5. An endoscopic biopsy forceps according to claim 4, wherein:

said first sliding member throughbore has a ramped entrance, said mating sleeve has a tapered proximal end, wherein upon insertion of said mating sleeve into said first coupling means, said tapered proximal end engages said ramped entrance and moves said first sliding member against said spring.

6. An endoscopic biopsy forceps according to claim 5, wherein:

said first sliding member includes manually operable means for moving said first sliding member against said spring to move said inner rim away from said groove and to permit uncoupling of said first mating means from said first coupling means.

7. An endoscopic biopsy forceps according to claim 2, wherein:

said handle includes a shaft and an annular movable member through which said shaft extends, said shaft having a transverse slot, and said shaft having an axial bore in its distal end, and said annular member having transverse member extending through said slot such that said annular movable member is captured by said shaft, and said first coupling means is located on said distal end of said shaft, and said proximal end of said flexible conduit and said proximal end of said pull wire are inserted into said axial bore of said shaft.

8. An endoscopic biopsy forceps according to claim 7, wherein:

said first coupling means includes extension means for extending said first coupling means proximal of said annular movable member.

9. An endoscopic biopsy forceps according to claim 8, wherein:

said extension means includes a finger flange at a proximal end thereof.

10. An endoscopic biopsy forceps according to claim 2, wherein:

said second coupling means is spring biased such that insertion of said second mating means into said second coupling means moves said second coupling means and couples said second mating means to said second coupling means.

11. An endoscopic biopsy forceps according to claim 10, wherein:

said handle includes a shaft and an annular movable member through which said shaft extends, said shaft having a transverse slot, said annular movable member having a transverse member extending through said slot such that said annular movable member is captured by said shaft, and said transverse member includes said second coupling means.

12. An endoscopic biopsy forceps according to claim 11, wherein:

said second coupling means comprises at least one moving member having a catching lip and a spring which biases said moving member transverse said second mating means, and said second mating means includes a tapered mating tip having a groove behind said tapered mating tip, wherein said catching lip mates in said groove.

13. An endoscopic biopsy forceps according to claim 12, wherein:

said moving member is a sliding member which slides transverse said second mating means, said catching lip has a tapered surface which terminates in a shoulder, wherein said tapered mating tip when contacting said tapered surface overcomes the bias provided by said spring and moves said sliding member transversely, and when said tapered mating tip passes by said tapered surface, said shoulder mates with said groove.

14. An endoscopic biopsy forceps according to claim 12, wherein:

said moving member has a tang extending parallel to said pull wire, said tang having a tapered surface, and said distal end of said shaft slot includes an engaging edge aligned with said tapered surface of said tang such that axial movement of said tapered surface of said tang into engagement with said engaging edge of said shaft slot overcomes the bias provided by said spring and moves said sliding member transversely.

15. An endoscopic biopsy forceps according to claim 12, wherein:

said moving member having a catching lip comprises a hinged arm which is hinged to said movable member distally of said spring, and said catching lip has a tapered surface which terminates in a shoulder, wherein said tapered mating tip when contacting said tapered surface overcomes the bias provided by said spring and moves said catching lip transversely, and when said tapered mating tip passes by said tapered surface, said shoulder mates with said groove.

16. An endoscopic biopsy forceps according to claim 15, wherein:

said distal end of said shaft slot includes an engaging edge aligned with said arm such that axial movement of said arm into engagement with said engaging edge of said shaft slot overcomes the bias provided by said spring and moves said catching lip transversely.

17. An endoscopic biopsy forceps according to claim 12, wherein:

said sliding member has a tang extending parallel to said pull wire, said tang having a tapered surface, and said annular movable member has a spring loaded collar in its annulus, said spring loaded collar having a proximal tapered surface aligned with said tapered surface of said tang such that axial movement of said proximal tapered surface of said collar overcomes the bias provided by said spring and moves said sliding member transversely.

18. An endoscopic biopsy forceps according to claim 17, further comprising:

a second spring which spring loads said spring loaded collar distally, and said shaft includes a release shoulder distal said annular movable member, said release shoulder aligned with the distal surface of said spring loaded collar to contact said spring loaded collar when said annular movable member is moved distally.

19. An endoscopic biopsy forceps according to claim 17, wherein:

said first coupling means includes extension means for extending said first coupling means proximal of said annular movable member, and said extension means includes a radial protrusion on its outer surface and distal said annular movable member which engages said collar to uncouple said second mating means and said second coupling means.

20. An endoscopic biopsy forceps according to claim 1, wherein:

said second mating means is spring biased.

21. An endoscopic biopsy forceps according to claim 20, wherein:

said first mating means comprises a sleeve which receives said flexible conduit, said sleeve having at least one resilient external arm terminating in a resilient barb, and said first coupling means comprises a lip on said handle having an angled entry through which said resilient barb can be forced, and an annular space proximal said angled entry which receives said resilient barb.

22. An endoscopic biopsy forceps according to claim 21, wherein:

said resilient external arm of said sleeve includes a finger grip indentation which when squeezed cause said resilient barb to disengage from said annular space.

23. In an endoscopic biopsy forceps having a jaw coupled to a distal end of a flexible conduit and a pull wire coupled to the jaw and extending through the conduit for opening and closing the jaw and a handle coupled to a proximal end of the conduit, the handle having actuating means coupled to a proximal end of the pull wire for moving the pull wire through the conduit to open and close the jaw, the improvement means for rapidly coupling and uncoupling the pull wire and conduit to the handle, said means for rapidly coupling and uncoupling comprising, a) first mating means for mating with a coupling means attached to the proximal end of the conduit;

b) second mating means for mating with a coupling means attached to the proximal end of the pull wire;

c) first coupling means for releasingly coupling with said first mating means, said first coupling means attached to a distal end of the handle; and d) second coupling means for releasingly coupling with said second mating means, said second coupling means located on the handle, wherein, one of said first mating means and said first coupling means is spring biased, and one of said second mating means and said second coupling means is spring biased, such that insertion of the proximal end of the flexible conduit and the proximal end of the pull wire into the handle automatically couples said first mating means to said first coupling means and said second mating means is automatically coupled to said second coupling means upon one of said insertion and movement of the actuating means.

24. In an endoscopic biopsy forceps according to claim 23, wherein:

said first coupling means is spring biased such that insertion of said first mating means into said first coupling means moves said first coupling means and couples said first mating means to said first coupling means.

25. In an endoscopic biopsy forceps according to claim 24, wherein:

said first coupling means includes, a first sliding member having a throughbore which receives said first mating means, said throughbore having an inner rim, a body member having a central throughbore which receives said first mating means, and a channel which holds said first sliding member, a spring which biases said first sliding member relative to said body member so that said inner rim partially obstructs said central throughbore of said body member, and wherein said first mating means comprises a sleeve having a circumferential groove which engages said inner rim.

said first sliding member throughbore has a ramped entrance, said mating sleeve has a tapered proximal end, wherein upon insertion of said mating sleeve into said first coupling means, said tapered proximal end engages said ramped entrance and moves said first sliding member against said spring.

26. In an endoscopic biopsy forceps according to claim 25, wherein:

said first sliding member includes manually operable means for moving said first sliding member against said spring to move said inner rim away from said groove and to permit uncoupling of said first mating means from said first coupling means.

27. In an endoscopic biopsy forceps according to claim 24, wherein:

the handle includes a shaft and an annular movable member through which said shaft extends, said shaft having a transverse slot, said annular movable member having a transverse member extending through said slot such that said annular movable member is captured by said shaft, said transverse member includes said second coupling means, and said second coupling means comprises at least one leaf spring, and said second mating means includes a mating tip with a distal portion of smaller diameter than a proximal portion of said mating tip, wherein said leaf spring is bendable by said mating tip and engages said mating tip distal of said proximal portion of said mating tip.

28. In an endoscopic biopsy forceps according to claim 23, wherein:

the handle includes a shaft and an annular movable member through which said shaft extends, said shaft having a transverse slot, and said shaft having an axial bore in its distal end, and said annular member having a transverse member extending through said slot such that said annular movable member is captured by said shaft, and said first coupling means is located on said distal end of said shaft, and the proximal end of the flexible conduit and the proximal end of the pull wire are inserted into said axial bore of said shaft.

29. In an endoscopic biopsy forceps according to claim 28, wherein:

said first coupling means includes extension means for extending said first coupling means proximal of said annular movable member, and said extension means includes a finger flange at a proximal end thereof.

30. In an endoscopic biopsy forceps according to claim 23, wherein:

said second coupling means is spring biased such that insertion of said second mating means into said second coupling means moves said second coupling means and couples said second mating means to said second coupling means, the handle includes a shaft and an annular movable member through which said shaft extends, said shaft having a transverse slot, said annular movable member having a transverse member extending through said slot such that said annular movable member is captured by said shaft, and said transverse member includes said second coupling means.

31. In an endoscopic biopsy forceps according to claim 30, wherein:

said second coupling means comprises at least one moving member having a catching lip and a spring which biases said moving member transverse said second mating means, and said second mating means includes a tapered mating tip having a groove behind said tapered mating tip, wherein said catching lip mates in said groove.

32. In an endoscopic biopsy forceps according to claim 31, wherein:

said moving member is a sliding member which slides transverse said second mating means, said catching lip has a tapered surface which terminates in a shoulder, wherein said tapered mating tip when contacting said tapered surface overcomes the bias provided by said spring and moves said sliding member transversely, and when said tapered mating tip passes by said tapered surface, said shoulder mates with said groove.

33. In an endoscopic biopsy forceps according to claim 31, wherein:

the sliding member has a tang extending parallel to said pull wire, said tang having a tapered surface, and said annular movable member has a spring loaded collar in its annulus, said spring loaded collar having a proximal tapered surface aligned with said tapered surface of said tang such that axial movement of said proximal tapered surface of said collar overcomes the bias provided by said spring and moves said sliding member transversely, said means for rapidly coupling and uncoupling further comprising a second spring which spring loads said spring loaded collar distally, and said shaft includes a release shoulder distal said annular movable member, said release shoulder aligned with the distal surface of said spring loaded collar to contact said spring loaded collar when said annular movable member is moved distally.

34. In an endoscopic biopsy forceps according to claim 31, wherein:

the sliding member has a tang extending parallel to said pull wire, said tang having a tapered surface, and said distal end of said shaft slot includes an engaging edge aligned with said tapered surface of said tang such that axial movement of said tapered surface of said tang into engagement with said engaging edge of said shaft slot overcomes the bias provided by said spring and moves said sliding member transversely.

35. In an endoscopic biopsy forceps according to claim 31, wherein:

said moving member having a catching lip comprises a hinged arm which is hinged to said movable member distally of said spring, and said catching lip has a tapered surface which terminates in a shoulder, wherein said tapered mating tip when contacting said tapered surface overcomes the bias provided by said spring and moves said catching lip transversely, and when said tapered mating tip passes by said tapered surface, said shoulder mates with said groove.

36. In an endoscopic biopsy forceps according to claim 35, wherein:
said distal end of said shaft slot includes an engaging edge aligned with said arm such that axial movement of said arm into engagement with said engaging edge of said shaft slot overcomes the bias provided by said spring and moves said catching lip transversely.

37. In an endoscopic biopsy forceps according to claim 23, wherein:
said first mating means is spring biased and comprises a sleeve which receives the flexible conduit, said sleeve having at least one resilient external arm terminating in a resilient barb, and
said first coupling means comprises a lip on the handle having an angled entry through which said resilient barb can be forced, and an annular space proximal said angled entry which receives said resilient barb.

38. In an endoscopic biopsy forceps according to claim 37, wherein:
said resilient external arm of said sleeve includes a finger grip indentation which when squeezed cause said resilient barb to disengage from said annular space.

39. An apparatus for insertion into a handle of an endoscopic instrument, the handle having an actuating means for actuating said apparatus, the actuating means having a first coupling means for coupling to a mating means and a second coupling means for coupling to a mating means wherein the second coupling means is spring biased, said apparatus comprising:
a) a flexible conduit having a proximal and a distal end, said proximal end of said conduit being provided with a first mating means for releasably mating with the first coupling means;
b) a pair of jaws mounted at the distal end of said flexible conduit;
c) at least one pull wire having a proximal and a distal end, the distal end of said pull wire being coupled to said pair of jaws, said pull wire extending through said conduit and said proximal end of said pull wire extending beyond said proximal end of said conduit, movement of said pull wire through said conduit effecting opening and closing of said jaws, said proximal end of said pull wire being provided with a second mating means for releasably mating with the second coupling means, wherein
said first mating means is spring biased, such that insertion of said proximal end of said flexible conduit and said proximal end of said pull wire into the handle automatically couples said first mating means to the first coupling means such that the handle and said apparatus together form an endoscopic instrument which is ready for use.

40. An apparatus according to claim 39, wherein:
said second mating means includes a tapered mating tip having a groove behind said tapered mating tip.

41. An apparatus according to claim 39, wherein:
said first mating means comprises a sleeve which receives said flexible conduit, said sleeve having at least one resilient external arm terminating in a resilient barb.

42. An apparatus according to claim 41, wherein:
said resilient external arm of said sleeve includes a finger grip indentation.

43. A method for assembling an endoscopic instrument having a handle with an actuating means having a first coupling means and a second coupling means, and a distal portion having a conduit having a proximal and a distal end, said proximal end of said conduit being provided with a first mating means for releasably mating with said first coupling means, an end effector mounted at the distal end of said conduit, at least one wire having a proximal and a distal end, the distal end of said wire being coupled to said end effector, said wire extending through said conduit and said proximal end of said wire extending beyond said proximal end of said conduit, movement of said wire through said conduit effecting movement of said end effector, said proximal end of said wire being provided with a second mating means for releasably mating with said second coupling means, said method comprising:
inserting in a longitudinal motion said first mating means into mating engagement with said first coupling means whereupon said distal portion is thereby coupled to said handle and said second mating means is automatically coupled to said second coupling means upon one of said inserting and movement of said actuating means.

44. A method according to claim 43, further comprising:
providing one of said first mating means and said first coupling means with a spring bias, and one of said second mating means and said second coupling means with a spring bias.

45. An apparatus for insertion into a handle of an endoscopic instrument, the handle having an actuating means for actuating said apparatus, the actuating means having a first coupling means for coupling to a mating means and a second coupling means for coupling to a mating means wherein the first and second coupling means are spring biased, said apparatus comprising:
a) a flexible conduit having a proximal and a distal end, said proximal end of said conduit being provided with a first mating means for releasably mating with the first coupling means;
b) a pair of jaws mounted at the distal end of said flexible conduit;
c) at least one pull wire having a proximal and a distal end, the distal end of said pull wire being coupled to said pair of jaws, said pull wire extending through said conduit and said proximal end of said pull wire extending beyond said proximal end of said conduit, movement of said pull wire through said conduit effecting opening and closing of said jaws, said proximal end of said pull wire being provided with a second mating means for releasably mating with the second coupling means, such that
insertion of said proximal end of said flexible conduit and said proximal end of said pull wire into the handle automatically couples said first mating means to the first coupling means such that the handle and said apparatus together form an endoscopic instrument which is ready for use.

46. An apparatus according to claim 45, wherein:
said first mating means comprises a sleeve having a circumferential groove, said sleeve having a tapered proximal end, and
said second mating means includes a tapered mating tip having a groove behind said tapered mating tip.

47. An apparatus according to claim 45, wherein:

said first mating means comprises a sleeve having a circumferential groove.

48. An apparatus according to claim 47, wherein:

said sleeve has a tapered proximal end.

* * * * *